US00PP09384P

United States Patent [19]

Fuess

[11] Patent Number: Plant 9,384

[45] Date of Patent: Nov. 28, 1995

[54] CHRYSANTHEMUM PLANT NAMED 'EMPIRE VENTURA'

[76] Inventor: Janet S. Fuess, 22 Country Club Dr., New York Mills, N.Y. 13417-1456

[21] Appl. No.: 325,051

[22] Filed: Oct. 19, 1994

[51] Int. Cl.[6] ..... A01H 5/00

[52] U.S. Cl. ..... Plt./82.3

[58] Field of Search ..... Plt./82.2, 82.3, Plt./74.1

*Primary Examiner*—Howard J. Locker
*Attorney, Agent, or Firm*—Foley & Lardner

[57] ABSTRACT

A new and distinct cultivar of Chrysanthemum plant named Empire Ventura, characterized by its flat daisy capitulum form with two rows of bright yellow-orange ray florets, numerous disc florets, relatively small capitulum diameter, compact and semi-upright growth habit, and its adaptability to greenhouse or garden cultures.

1 Drawing Sheet

The present invention comprises a new and distinct cultivar of Chrysanthemum plant, botanically known as *Dendranthema grandiflora*, and hereinafter referred to by the cultivar name Empire Ventura.

Empire Ventura is a product of a planned breeding program which had the objective of creating new Chrysanthemum cultivars with freely branching and compact cushion habits, early flowering response, and daisy flowers with many ray florets, making it suitable for production as a garden variety.

Empire Ventura was originated from a hybridization made by the inventor Janet S. Fuess in a controlled breeding program in New Hartford, N.Y. in October 1990. The female parent was an unnamed seedling identified as E86-42 and described as an orange-bronze button.

The male parent of Emprie Ventura was Cornhusker, disclosed in U.S. Plant Pat. No. 6,401, an orange-bronze daisy garden mum.

Empire Ventura was discovered and selected as one flowering plant within the progeny of the stated parentage by the inventor in Sep. 1991, in a controlled environment in New Hartford, N.Y.

The first act of asexual reproduction of Empire Ventura was accomplished when vegetative cuttings were taken from the initial selection in October 1991 in a controlled environment in New Hartford, N.Y., by a technician working under formulations established and supervised by the inventor.

Horticultural examination of selected units initiated in September 1992 has demonstrated that the combination of characteristics as herein disclosed for Emprie Ventura are firmly fixed and are retained through successive generations of asexual reproduction.

Empire Ventura has not been observed under all possible environmental conditions. The phenotype may vary significantly with variations in environment such as temperature, light intensity and daylength, without, however, any variance in genotype.

The following observations, measurements and comparisons described plants grown in New Hartford, N.Y. under outdoor conditions which approximate those generally used in commercial practice.

The following traits have been repeatedly observed and are determined to be basic characteristics of Empire Ventura, which, in combination, distinguish this Chrysanthemum as a new and distinct cultivar:

1. Flat daisy capitulum form.
2. Two rows of ray florets, bright yellow-orange in color.

Semi-upright habit, suitable for production in 4" to 8" containers.

4. Flowers have an average of 33 ray florets and 148 disc florets.
5. Diameter across face of capitulum of 3.0–3.5 cm when fully open.
6. Fully expanded ray florets are approximately 1.5 cm long and 0.6 cm wide, with tridentate tips.
7. Natural season flowering date of September 25 in New Hartford, N.Y.
8. In a controlled Light/Shade Program, the new cultivar has a flowering response of 7 weeks.
9. Compact growth habit, with 7–9 branches per plant after pinch.
10. Adaptability to greenhouse or garden cultures.

Of the many commerical cultivars known to the present inventor, the most similar in comparison to Empire Ventura is Grace, disclosed in U.S. Plant Pat. No. 7,642. In comparison to Grace, Empire Ventura has a slightly smaller capitulum size, a more upright growth habit, shorter, more rounded ray florets, and a deeper yellow ray floret color. The seven week flowering response in Light/Shade Programs and the September 25 natural season flower date of Empire Venture are similar to those same characteristics of Grace.

The accompanying color photographic drawing shows typical inflorescence and foliage characteristics of Empire Ventura, with the colors being as nearly true as possible with illustrations of this type. The photograph comprises a top perspective view of a typical plant of Empire Ventura grown in an 8 inch pot.

In the following description, color references are made to The Royal Horticultural Society (R.H.S.) Colour Chart. The color vaules were determined between 10:00 a.m. and 1:00 p.m. on Sep. 8, 1994 under 4,000 footcandle at New Hartford, N.Y.

Classification:

*Botanical.*—*Dendranthema grandiflora* cv Empire Ventura.

*Commercial.*—Flat daisy garden mum.

Inflorescence

Capitulum:

*Form.*—Flat.

*Type.*—Daisy, with two rows of ray florets.

*Diameter across face.*—3.0–3.5 cm, when fully open.

Corolla of ray florets:

*Color (General tonality from a distance of three meters).*—Yellow-Orange.

*Color* (*Lower surface*).—22A.

*Color* (*Upper surface*).—15A.

Corolla of disc florets:

*Color* (*Mature*).—17A.

*Color* (*Immature*).—17B.

Reproductive organs:

*Androecium.*—Present on disc florets only; moderate pollen.

*Gynoecium.*—Present on both ray and disc florets. On ray florets, style is 0.5 cm and bifurcated; on disc florets, style is 0.4 cm, bifurcated, and enclosed in anther ring.

Plant

General appearance:

*Height.*—25–32 cm when grown in an 8 inch pot under natural daylength, with no growth regulators.

Foliage:

*Color* (*Lower surface*).—137B.

*Color* (*Upper surface*).—139A.

*Shape.*—Five-lobed, rounded; smooth margin with minute point at end of lobe, 4–5 cm long and 3.0–3.5 cm wide.

I claim:

1. A new and distinct cultivar of Chrysanthemum plant named Empire Ventura, as illustrated and described.

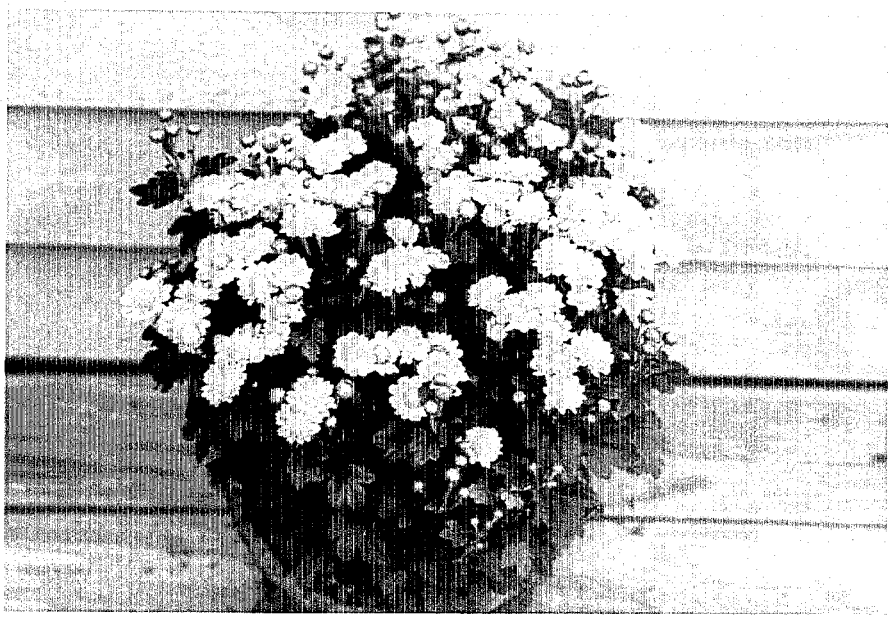

* * * * *